United States Patent [19]

Frank et al.

[11] Patent Number: 5,888,962
[45] Date of Patent: Mar. 30, 1999

[54] NITRILE PERFUMERY MATERIAL

[75] Inventors: Walter C. Frank, Holland, Pa.; Alex R. Pagano, Morris Township, N.J.

[73] Assignee: Bush Boake Allen Inc., Montvale, N.J.

[21] Appl. No.: 974,950

[22] Filed: Nov. 20, 1997

[51] Int. Cl.⁶ .............................. A61K 7/46; A61K 7/32; A61K 7/075; A61K 7/00
[52] U.S. Cl. ............................ 512/22; 424/65; 424/70.1; 424/401; 512/1; 512/6; 512/20
[58] Field of Search ............................. 512/1, 6, 20, 22; 424/65, 70.1, 401

[56] References Cited

U.S. PATENT DOCUMENTS 4,193,934  3/1980  Bauer et al. ........................ 260/465 R

*Primary Examiner*—Shelley A. Dodson
*Assistant Examiner*—Marina Lamm
*Attorney, Agent, or Firm*—Dechert Price & Rhoads

[57] ABSTRACT

The present invention relates to a perfumery material composed of a mixture of 3-methyl-5-phenyl-pentanenitrile and 3-methyl-5-cyclohexyl-pentanenitrile, which can be combined with other perfumery materials.

22 Claims, No Drawings

NITRILE PERFUMERY MATERIAL

The present invention relates to mixtures of nitrites, and to their use as perfumery material.

The invention relates to compositions of matter comprising Compound A, 3-methyl-5-phenyl-pentanenitrile:

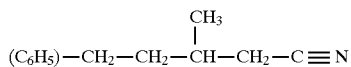

and Compound B, 3-methyl-5-cyclohexyl-pentanenitrile:

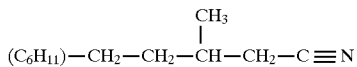

The perfumery materials according to the invention are distinguished by an enhanced citrus character, improved stability and superior masking abilities.

Numerous perfumery materials with citrus character are known in the art. For example, citral, Citralva™, citronellyl nitrile, and Citronitrile™ have a citrus odor. However, these materials are readily affected by hostile media, losing their fragrance and/or generating additional off notes.

Further, unsatisfactory fragrance stability can be associated with unsatisfactory chemical stability in media. The chemical degradation of a perfumery material can lead to loss of desired agents in the media. For example, the addition of citral to liquid bleach causes a decrease in active chlorine content and thereby a reduced efficacy of the bleach.

Other perfumery materials with a citrus character, such as geranic acid nitrile, Citrowanil B™, dihydromyrcenol, dihydromyrcenyl acetate, Dimetol™, Limetol™, Octacetal™, tetrahydromyrcenol, tetrahydromyrcenyl acetate, tetrahydrogeranyl nitrile, dihydrolimonene epoxide, dodecene-1, 2-epoxide, n-undecyl nitrile, 1-n-heptyl-1,3-dioxolane, 3,7-dimethyl-3-octanol, limonene, citral diethylacetal, and citral dimethylacetal, are less affected by hostile media. See, e.s., Laufer et al., U.S. Pat. No. 3,876,551, 6:25–32. However, such prior art perfumery materials in hostile media, particularly basic aggressive media, have a deficient citrus character, provide only an incomplete masking of other odors in the media, and/or have unsatisfactory fragrance stability.

It is known in the art that Compound A and Compound B are perfumery materials having a citrus character that can be used under specific conditions to provide fragrance to media. See Bauer et al., U.S. Pat. No. 4,193,934; Bauer et al., German Patent Application No. 2,348,359; Agostini et al., European Patent Publication No. 0622451; Sturm, Parfum. Kosmet. (1974) 55 (12), pp. 351–55.

Surprisingly, the present invention provides perfumery materials having improved fragrance stability, citrus character and masking ability in hostile media, as compared to Compound A or Compound B used individually as a perfumery material. The present invention offers an improved perfumery material with increased persistence of a pleasant citrus odor, lemon in character, and improved masking ability in hostile media.

SUMMARY OF THE INVENTION

The invention relates to a perfumery material comprising a mixture of 3-methyl-5-phenyl-pentanenitrile (Compound A) and 3-methyl-5-cyclohexyl-pentanenitrile (Compound B).

In one embodiment, the invention provides a perfumery material comprising a mixture of 3-methyl-5-phenyl-pentanenitrile and 3-methyl-5-cyclohexyl-pentanenitrile wherein the 3-methyl-5-cyclohexyl-pentanenitrile comprises less than about 50% of the mixture by weight. Preferably, the invention provides a perfumery material comprising a mixture of 3-methyl-5-phenyl-pentanenitrile and 3-methyl-5-cyclohexyl-pentanenitrile wherein the 3-methyl-5-cyclohexyl-pentanenitrile comprises between about 0.01% and about 25% of the mixture by weight; more preferably, between about 0.5% and about 20% of the mixture by weight; still more preferably, between about 1% and about 10% of the mixture by weight.

In another embodiment, the invention provides a perfumery material comprising a mixture of 3-methyl-5-phenyl-pentanenitrile and 3-methyl-5-cyclohexyl-pentanenitrile wherein the 3-methyl-5-cyclohexyl-pentanenitrile comprises between about 4% and about 6% of the mixture by weight.

In a further embodiment, the perfumery material exists in medium. In another embodiment, the medium is hostile. The hostile medium can be aggressive, or oxidative, or both. The aggressive medium can be acidic or basic. The oxidative medium can comprise, but is not limited to, at least one of hypochlorite, hydrogen peroxide, chlorine dioxide, chlorinated hydantoin, brominated hydantoin, peroxy acid salts, sodium perborate, sodium percarbonate, dichloro isocyanurate, and trichloro isocyanurate.

The invention also provides the use of a perfumery material to provide a fragrance, either alone or in combination with other compounds. The use to provide a fragrance can be in a medium, particularly, a hostile medium such as an aggressive medium, and/or an oxidative medium. As above, the aggressive medium can be acidic or basic, and the oxidative medium can comprise, but is not limited to, at least one of hypochlorite, hydrogen peroxide, chlorine dioxide, chlorinated hydantoin, brominated hydantoin, peroxy acid salts, sodium perborate, sodium percarbonate, dichloro isocyanurate, and trichloro isocyanurate.

DEFINITIONS

The following terms shall have, for the purposes of this application, the respective meanings set forth below. In particular, for the purpose of interpreting the claims, the term definitions shall control over any assertion of a contrary meaning based on other text found herein:

Aggressive media or medium—Media or medium having a pH less than about 5 or greater than about 9.

Chemical Stability—Maintenance of the chemical structure of a perfumery material.

Citrus character—Component of a fragrance that resembles the odor of citrus fruit(s), e.g., lemons, oranges, and limes.

Fragrance—The odor of a composition of matter.

Fragrance Stability—Persistence and constancy of the odor of a perfumery material.

Hostile media or medium—Media or medium which is aggressive, or oxidative, or both.

Masking ability—The ability of a composition of matter, when added to a mixture, to disguise or cover up a pre-existing odor in the mixture.

Media or medium—A non-gaseous composition of matter comprised of one or more compounds.

Oxidative media or medium—Media or medium having an oxidative potential approximately greater than about −0.6 volts relative to a standard hydrogen electrode, in standard conditions. See Biermann et al., Prog. Pap. Recycl. (1997) 6, p. 65.

Perfumery material—A composition of matter with an odor.

DETAILED DESCRIPTION OF THE INVENTION

The present invention is directed to, among other things, a perfumery material comprising a mixture of Compound A and Compound B. Compound A is 3-methyl-5-phenyl-pentanenitrile and Compound B is 3-methyl-5-cyclohexyl-pentanenitrile.

Methods of production of these compounds are known in the art. For example, see Bauer et al., U.S. Pat. No. 4,193,934, and Bauer et al., German Patent Application No. 2348359. Mixtures of varying proportions of Compound A and Compound B can be obtained by combining the two types of compounds by conventional means, known to those skilled in the art. See, e.g., Müller et al.,eds., *Perfumes: Art. Science and Technology* (1991), pp.421–440.

In a preferred embodiment of the invention, Compound B is the minor component of the perfumery material, comprising less than 50% of the composition by weight. Preferably, the perfumery material comprises Compound B between about 0.01% and about 25% by weight. More preferably, the perfumery material comprises Compound B between about 0.5% and about 20% by weight. Still more preferably, the perfumery material comprises Compound B between about 1% and about 10% by weight. Yet more preferably, the perfumery material comprises Compound B between about 4% and about 6% by weight.

The perfumery material of the invention can be used to provide a fragrance in isolation, or in combination with other perfumery material known in the art, such as aliphatic aldehydes, including, but not limited to, octyl, nonyl, decyl and undecylenic aldehydes; aliphatic alcohols, including, but not limited to, octyl, nonyl and decyl alcohols, 9-decen-1-ol, and 3, 5, 5-trimethylhexanol; terpene alcohols, including, but not limited to, geraniol, citronellol, α-terpineol, dihydroterpineol, tetrahydrogeraniol, linalool, tetrahydromyrcenol, and dihydromyrcenol; terpene esters, including, but not limited to, geranyl acetate, citronellyl acetate, terpinyl acetate, dihydroterpinyl acetate, tetrahydrogeranyl acetate, linalyl acetate, tetrahydrolinalyl acetate, tetrahydromyrcenyl acetate, dihydromyrcenyl acetate; musks, including, but not limited to, Abbalide™, Tetralide™, Habanolide™, Exaltolide™, Musk R-1™, Attractolide™, Ambreton™, and ethylene brassylate; and other perfumery materials, including, but not limited to, ortho-tertiary-butylcyclohexyl acetate, para-tertiary-butylcyclohexyl acetate, methyl dihydrojasmonate, tridecene-2-nitrile, 2-methyl-decanonitrile, 3-methyl-decanonitrile, ethyl-2-methyl pentanone, Florosa™, and Polysantol™. See also Arctander, *Perfume and Flavor Chemicals*, Vols. I–II (1969); van der Weerdt et al., U.S. Pat. No. 4,459,224, 2:48–3:9.

The perfumery material can be used either in isolation or in a variety of media, both hostile and non-hostile. Hostile media include, but are not limited to, basic aggressive media such as soaps, laundry detergents, bleaches, automatic dishwashing agents, scouring powders, semi-permanent hair color products; acidic aggressive media such as fabric softeners, deodorants, antiperspirants, and cleaners containing citric acid, hydrochloric acid, sulfonic acid or phosphoric acid; and oxidative media, such as permanent hair colors and bleaches. Non-hostile media include alcoholic solutions, shampoos, hair conditioners, bath oils, lotions, gel-based air fresheners, cosmetics and tenside soaps. It is known to one skilled in the art which perfumery materials and media are suitable to be used in combination with the perfumery material of the invention. See e.g., Müller et al., eds., *Perfumes: Art, Science and Technology*, (1991) pp.348–382; *Encyclopedia of Chemical Technology*, 4th ed., Vol. 12 (1996), pp.178–181, 881–918.

As is apparent from these examples, the perfumery material of the invention can be used in a variety of cleansing products, for household and commercial applications, including bleaches, laundry detergents, dishwasher detergents, stain removers, fabric softeners, scouring agents, hand and body soaps, general and specific cleansers, in various forms, including liquids, gels, sprays, bars, sticks and powders. The perfumery material can be used in a variety of personal care products, including shampoos, dyes, permanent wave products, lotions, powders and deodorants. The perfumery material can also be used in other household products, including polishes, room fresheners, animal litters and deodorizers.

The amount of perfumery material of the invention, alone or with other perfumery materials, that can be used to provide a fragrance in a perfumed product varies depending on the nature of the perfumed product, and the intensity of the fragrance desired, which factors are apparent to one skilled in the art. In a preferred embodiment of the invention, the perfumery material is present in the medium between about 0.1% and about 50% by weight. Preferably, the perfumery material is present between about 1% and about 15% by weight, and even more preferably, between about 5% and about 15% by weight.

Preferably, the addition of the perfumery material of the invention causes a loss of the active agent of the media no greater than 20%, and still more preferably, no greater than 10%.

Surprisingly, the perfumery materials of the invention have improved fragrance stability as compared to Compound A and Compound B in isolation, improved lemon character and improved masking ability, without any reduction of chemical stability.

The following examples further illustrate the present invention, but should not be construed as in any way limiting its scope.

EXAMPLE 1

This example illustrates the fragrance stability in liquid bleach of the perfumery materials of the invention.

Perfumery materials in the mixtures shown in Chart 1 were added to a liquid bleach solution composed of 5% by weight sodium hypochlorite and 95% by weight water, adjusted to a pH of about 11.5 to about 12.0 by the addition of sodium hydroxide. The materials were added in the amount of 0.1% by weight. The odors of the individual mixtures in the bleach solution were evaluated organoleptically by one skilled in the art of fragrance detection and evaluation. The mixtures were then divided into two aliquots, one stored at about 70° F., and the other about 110° F., for ten (10) days.

After ten (10) days, the relative fragrance stability of the solutions was assayed by organoleptic evaluation of the solutions by one skilled in the art of fragrance detection and evaluation, using the key described in Chart 1. The relative character of the odor and coverage of bleach odor was also noted for solutions stored at 100° F.

The data show that the fragrance of tested perfumery materials of the invention are acceptably stable or stable and that the perfumery materials of the invention possess better lemon character and masking ability in liquid bleach than Compound A or B in isolation.

Chart 1
Fragrance Stability

| Weight Ratio of Compound B to Compound A | 70° F. | 100° F. | Characters |
| --- | --- | --- | --- |
| 10/990 | A | A− | less lemon character, good coverage. |
| 20/980 | A | A− | less lemon character, good coverage |
| 50/950 | A | A | best lemon character, best coverage |
| 100/900 | A | A− | less lemon character, good coverage |
| 250/750 | A | B | less lemon character, least coverage |
| 0/1000 | A | B+ | less lemon character, slightly less coverage |
| 1000/0 | A | A− | less lemon character, slightly green - spicy |

Key: A - Stable; B - Acceptably stable, slight change; C - Unstable, not disagreeable; D - Unstable, "off" odor.

EXAMPLE 2

This example illustrates the chemical stability of the perfumery materials of the invention in liquid bleach.

Perfumery materials in the mixtures shown in Chart 2 were added to a liquid bleach solution composed of 5% by weight sodium hypochlorite and 95% water, adjusted to a pH of about 11.5 to 12.0 by the addition of sodium hydroxide, with an initial chlorine concentration of 5.04% by weight. The materials were added to 0.1% by weight. Each sample was divided into two aliquots, one stored at about 70° F. and the other at about 110° F. for ten (10) days.

After ten (10) days, the chlorine concentration of the mixtures was determined using the method disclosed below, with the results as shown in Chart 2.

Active chlorine content was measured by titration. 0.5 g of the sample solution was added to a mixture of 2.5 g potassium iodide, 50 g distilled water, and 10 ml glacial acetic acid. While stirring vigorously, 0.1N sodium thiosulfate solution was gradually added to the mixture. When the mixture turned clear, and persisted as a clear solution, the titration was finished. The weight percent active chlorine content was calculated by multiplying the volume of sodium thiosulfate solution added in milliliters by the normality of the sodium thiosulfate solution, by a factor, 0.037222, derived from the equivalent weight of sodium hypochlorite, and by 100, and dividing by the weight of the initial sample mixture. See Fritz et al., *Quantitative Analytical Chemistry*, 2nd ed. (1969), 101–118, 239–284.

The loss of active chlorine content in bleach solutions containing the materials of the invention, as in solutions containing Compound A and Compound B alone, is less than 20%, showing acceptable chemical stability of the perfumery material in liquid bleach.

Chart 2
Active Chlorine Content (%) After Ten Days

| Weight Ratio of Compound B to Compound A | 70° F. | 100° F. |
| --- | --- | --- |
| 10/990 | 4.98 | 4.55 |
| 20/980 | 4.87 | 4.67 |
| 50/950 | 4.87 | 4.53 |
| 100/900 | 4.83 | 4.58 |
| 250/950 | 4.73 | 4.69 |
| 0/1000 | 4.81 | 4.59 |
| 1000/0 | 4.78 | 4.73 |
| 0/0 | 4.89 | 4.88 |

Initial active chlorine content = 5.04% by weight

EXAMPLE 3

This example illustrates the chemical stability of the perfumery materials of the invention in hydrogen peroxide solution.

Perfumery materials in the mixtures shown in Chart 3 were added to a hydrogen peroxide solution with an initial concentration of $H_2O_2$ of 3.40% by weight, and an initial pH between about 11.5 and about 12. The materials were added to 0.1% by weight. Each sample was divided into two aliquots, one stored at about 70° F. and the other at about 110° F. for one month. After one month, the hydrogen peroxide concentration of the mixtures was determined, using the method described below, with the results as shown in Chart 3.

Hydrogen peroxide concentration was measured by titration. 5g of the sample mixture was mixed with 50 g of 25% by weight sulfuric acid solution. While stirring vigorously, 0.5N potassium permanganate was gradually added to the mixture. When the mixture turned faintly pink in color, and the color persisted for one minute, the titration was finished. The concentration of hydrogren peroxide as percentage by weight was calculated by multiplying the number of milliliters of potassium permanganate solution added by the normality of the potassium permanganate solution, by a factor, 1.701, derived from the equivalent weight of hydrogen peroxide, and dividing by the weight of the initial sample mixture. See Fritz et al., *Quantitative Analytical Chemistry*, 2nd ed. (1969), 101–118, 239–284.

The loss of hydrogen peroxide in solutions containing the materials of the invention, as in solutions containing Compound A and Compound B alone, is less than 20%, showing acceptable chemical stability of the perfumery material in hydrogen peroxide solutions.

Chart 3
Concentration of $H_2O_2$ (%) After One Month

| Weight Ratio of Compound B to Compound A | 70° F. | 100° F. |
| --- | --- | --- |
| 10/990 | 3.32 | 3.32 |
| 20/980 | 3.15 | 3.15 |
| 50/950 | 3.32 | 3.15 |
| 100/900 | 3.23 | 3.23 |
| 250/750 | 3.32 | 3.23 |
| 0/1000 | 3.32 | 3.23 |
| 1000/0 | 3.40 | 3.32 |
| 0/0 | 3.40 | 3.23 |

Initial $H_2O_2$ concentration = 3.40% by weight

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A perfumery material comprising a mixture of a compound of 3-methyl-5-phenyl-pentanenitrile (Compound A) and 3-methyl-5-cyclohexyl-pentanenitrile (Compound B).

2. The perfumery material of claim 1, wherein Compound B comprises more than about 0.01% and less than 500% of the mixture by weight.

3. The perfumery material of claim 1 wherein Compound B comprises between about 0.01% and about 25% by weight.

4. The perfumery material of claim 1 wherein Compound B comprises between about 0.5% and about 20% by weight.

5. The perfumery material of claim 1 wherein Compound B comprises between about 1% and about 10% by weight.

6. The perfumery material of claim 1 wherein Compound B comprises between about 4% and about 6% by weight.

7. The perfumery material of claim 1 in a medium.

8. The perfumery material of claim 7 wherein the medium is hostile.

9. The perfumery material of claim 8 wherein the medium is aggressive.

10. The perfumery material of claim 8 wherein the medium is oxidative.

11. The perfumery material of claim 9 wherein the medium is acidic.

12. The perfumery material of claim 9 wherein the medium is basic.

13. The perfumery material of claim 10 wherein the oxidative medium comprises one or more compounds selected from the group comprising hypochlorite, hydrogen peroxide, chlorine dioxide, chlorinated hydantoin, brominated hydantoin, peroxy acid salts, sodium perborate, sodium percarbonate, dichloro isocyanurate, and trichloro isocyanurate.

14. A method for obtaining a fragrance comprising employing the perfumery material of claim 1 to provide an odor.

15. A method for obtaining a fragrance comprising employing the perfumery material of claim 1 in combination with at least one other perfumery material to provide an odor.

16. A method for obtaining a fragrance in a medium comprising employing the perfumery material of claim 1 in the medium to provide an odor.

17. The method of claim 16 wherein the medium is hostile.

18. The method of claim 17 wherein the medium is aggressive.

19. The method of claim 17 wherein the medium is oxidative.

20. The method of claim 18 wherein the medium is acidic.

21. The method of claim 18 wherein the medium is basic.

22. The method of claim 19 wherein the medium comprises one or more compounds selected from the group comprising hypochlorite, hydrogen peroxide, chlorine dioxide, chlorinated hydantoin, brominated hydantoin, peroxy acid salts, sodium perborate, sodium percarbonate, dichloro isocyanurate, and trichloro isocyanurate.

* * * * *